(12) United States Patent
Boege et al.

(10) Patent No.: US 7,289,217 B2
(45) Date of Patent: Oct. 30, 2007

(54) FLUORESCENT DETECTOR WITH AUTOMATIC CHANGING FILTERS

(75) Inventors: Steven J. Boege, San Mateo, CA (US); Mark F. Oldham, Los Gatos, CA (US); Liana Ilkova, Sunnyvale, CA (US)

(73) Assignee: Applera Corporation, Foster City, CA (US)

( * ) Notice: Subject to any disclaimer, the term of this patent is extended or adjusted under 35 U.S.C. 154(b) by 241 days.

(21) Appl. No.: 10/929,320

(22) Filed: Aug. 30, 2004

(65) Prior Publication Data

US 2005/0190366 A1  Sep. 1, 2005

Related U.S. Application Data

(63) Continuation-in-part of application No. 10/758,667, filed on Jan. 14, 2004.

(51) Int. Cl.
*G01N 21/25* (2006.01)

(52) U.S. Cl. .................................................. 356/417

(58) Field of Classification Search ................ 356/417, 356/418; 250/458.1, 461.2
See application file for complete search history.

(56) References Cited

U.S. PATENT DOCUMENTS

| | | | |
|---|---|---|---|
| 4,972,258 A | | 11/1990 | Wolf et al. |
| 5,943,129 A | * | 8/1999 | Hoyt et al. ................. 356/318 |
| 6,225,636 B1 | | 5/2001 | Ginestet |
| 6,320,660 B1 | * | 11/2001 | Ju et al. ...................... 356/417 |
| 6,333,501 B1 | * | 12/2001 | Labrenz .................... 250/341.5 |
| 6,518,068 B1 | * | 2/2003 | Gambini et al. .............. 436/50 |
| 6,534,308 B1 | | 3/2003 | Palsson et al. |
| 6,633,662 B2 | | 10/2003 | Ravkin |
| 6,829,051 B2 | * | 12/2004 | Abe et al. .................... 356/417 |
| 7,050,224 B2 | * | 5/2006 | Kawamata et al. .......... 359/359 |
| 2003/0011772 A1 | * | 1/2003 | Abe et al. .................... 356/417 |
| 2003/0148505 A1 | | 8/2003 | Gambini et al. |
| 2004/0066510 A1 | | 4/2004 | Hoff et al. |
| 2004/0072335 A1 | * | 4/2004 | Boege et al. .............. 435/287.2 |

FOREIGN PATENT DOCUMENTS

| | | |
|---|---|---|
| EP | 0 987 540 A2 | 3/2000 |
| EP | 1 411 345 A1 | 4/2004 |
| JP | 10221242 | 8/1998 |
| JP | 2001083090 | 3/2001 |
| JP | 2002014044 | 1/2002 |
| WO | WO 99/60381 | 11/1999 |
| WO | WO 01/07896 A1 | 2/2001 |

OTHER PUBLICATIONS

"Fluorescence Microscopy Reflected Light," http: /micro.magnet.fsu.edu/primer/techniques/fluorescence/reflectlightpaths.html.

Lee et al., "Seven-Color, Homogeneous Detection of Six PCR Product," Research Report, BioTechniques, vol. 27, No. 2 (1999) pp. 342-349.

International Search Report from International application No. PCT/US2005/001485 date of mailing Aug. 29, 2005, along with Written Opinion of the ISA.

\* cited by examiner

*Primary Examiner*—Roy M. Punnoose

(57) ABSTRACT

A fluorometry device and method adapted to determine concentration of spectrally distinguishable species in a biological sample with a plurality of movable optical devices.

8 Claims, 7 Drawing Sheets

FLUORESCENT DETECTOR WITH AUTOMATIC CHANGING FILTERS

CROSS-REFERENCE TO RELATED APPLICATIONS

This application is a continuation-in-part of U.S. patent application Ser. No. 10/758,667, filed Jan. 14 2004, which is incorporated herein by reference.

FIELD

The present teaching relates to methods and systems for fluorescent detection in biological samples.

INTRODUCTION

Polymerase chain reaction (PCR) is a process for amplifying or multiplying quantities of double-stranded deoxyribonucleic acid (DNA) in a sample. Measurements can be taken, in situ, to monitor the performance of the PCR process. One measurement technique is microscopy. Microscopy can be used to spacially resolve features of interest in the DNA content of the sample based on dyes that fluoresce in the presence of DNA. However, microscopy systems are limited to viewing only one depth of view of the sample at a time, and thus, are unsuitable for making quantitative measurements, such as a concentration measurement.

Another measuring technique is fluorometry. Fluorometry utilizes microvolume fluorometers (spectofluorometers) to spectrally resolve fluorescent light from the volume of biological sample to provide quantitative measurements such as concentration. Fluorometers can illuminate the sample and utilize dyes that fluoresce in the presence of DNA. The light that fluoresces from a dye can be quantitatively measured using an optical device and a detector without collimating the light through the optical device and without focusing the light from the sample on the detector.

High-throughput systems can provide DNA amplification of multiple samples in parallel, such as in a microwell tray or microcard. Assays can provide multiple DNA target sequences of interest, such as diagnostic assays, for example, HIV screening. These assays can provide multiple spectrally distinguishable species, such as different fluorescent dyes, in each of the multiple samples thermally cycled in parallel.

However, light emitted from the samples or the light source typically contains spatial non-uniformities. These spatial non-uniformities can be caused by diffraction or irregularities in emission. The non-uniformities can make it difficult to resolve the various features or to accurately determine the concentration of a given material in a sample. It is desirable, therefore, to have a system capable of solving the problems encountered by spatial non-uniformites.

SUMMARY

According to various embodiments, the present teachings can provide an optical device for fluorometry to monitor a biological sample, the device including a first filter to condition an excitation light directed at a sample region, a beamsplitter positioned along a first optical axis, the first optical axis being an optical axis of the excitation light, and the beamsplitter positioned along a second optical axis, the second optical axis being an optical axis of an emission light, and a first optical element positioned along the second optical axis to collimate the emission light and to reduce non-uniformities in the emission light prior to the emission light impinging the beamsplitter.

According to various embodiments, the present teachings can provide a method of fluorometry to monitor a biological sample including providing a sample region including a sample tray and a plurality of wells, wherein each of the wells includes a sample, providing a first filter to condition an excitation light, and providing a first optical element to reduce non-uniformities in an emission light of the samples so that the emission light impinging a detector will be uniform for samples in different wells that have a similar volume of material, a similar concentration of material, and a similar dye.

It is to be understood that both the foregoing general description and the following detailed description are exemplary and explanatory only and are not restrictive of the invention as claimed.

The accompanying drawings, which are incorporated in and constitute a part of this specification, illustrate some embodiments of the invention, and together with the description serve to explain the principles of the invention.

DESCRIPTION OF VARIOUS EMBODIMENTS

Figure 1:
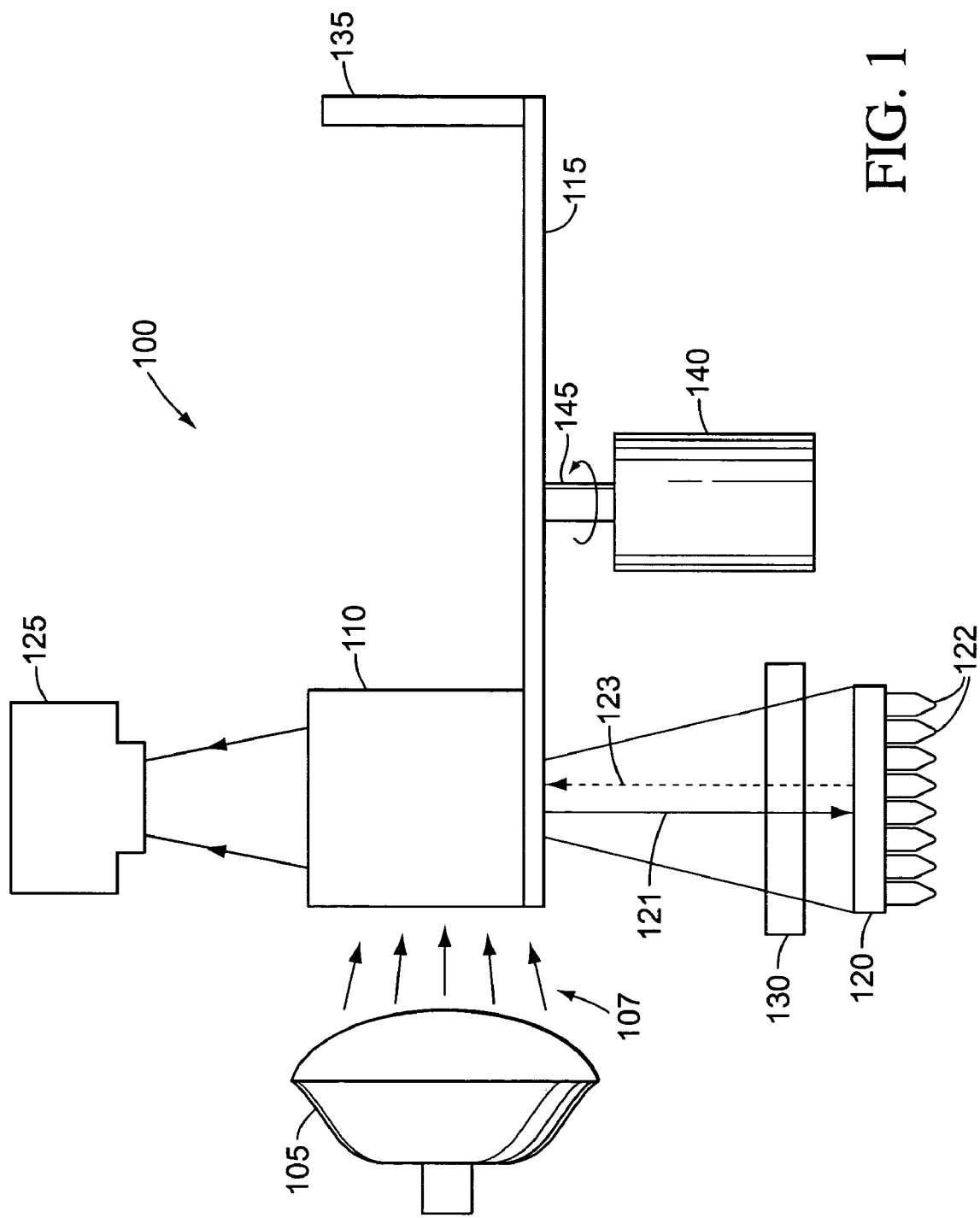
FIG. 1 illustrates a representative fluorometry system.

Reference will now be made in detail to some embodiments of the invention, examples of which are illustrated in the accompanying drawings. Wherever possible, the same reference numbers will be used throughout the drawings to refer to the same or like parts.

The term "light source" as used herein refers to a source of irradiance that can provide excitation that results in fluorescent emission. Light sources can include, but are not limited to, white light, halogen lamp, lasers, solid state laser, laser diode, micro-wire laser, diode solid state lasers (DSSL), vertical-cavity surface-emitting lasers (VCSEL), LEDs, phosphor coated LEDs, organic LEDs (OLED), thin-film electroluminescent devices (TFELD), phosphorescent OLEDs (PHOLED), inorganic-organic LEDs, LEDs using quantum dot technology, LED arrays, an ensemble of LEDs, a floodlight system using LEDs, and/or white LEDs, filament lamps, arc lamps, gas lamps, and fluorescent tubes. Light sources can have high irradiance, such as lasers, or low irradiance, such as LEDs. The different types of LEDs mentioned above can have a medium to high irradiance.

The term "detector" as used herein refers to any component, portion thereof, or system of components that can detect light including a charged coupled device (CCD), back-side thin-cooled CCD, front-side illuminated CCD, a CCD array, a photodiode, a photodiode array, a photomultiplier tube (PMT), a PMT array, complimentary metal-oxide semiconductor (CMOS) sensors, CMOS arrays, a charge-injection device (CID), CID arrays, etc. The detector can be adapted to relay information to a data collection device for storage, correlation, and/or manipulation of data, for example, a computer, or other signal processing system.

The term "sample volume" as used herein refers to the sample in any structure, such as a sample region or chamber, that provides containment to the sample. The sample volume can be open or transparent to provide entry to excitation light and exit to fluorescent light. The transparency can comprise glass, plastic, fused silica, etc. Further, the sample region can take any shape including a well, a tube, a vial, a cuvette, a tray, a multi-well tray, a microcard, a microslide, a capillary, an etched channel plate, a molded channel plate, an embossed channel plate, etc. The sample region can be part of a combination of multiple sample regions grouped into a row, an array, an assembly, etc. Multi-chamber arrays can include 12, 24, 36, 48, 96, 192, 384, or more, sample chambers. An exemplary sample chamber can be shaped to a multi-well tray under the SBS microtiter format.

The term "sample" as used herein refers to any biological or chemical substance in solution with components that can be excited by excitation light to emit fluorescent light. The sample can include one or more nucleic acid sequences to be amplified and/or sequenced. The sample can include reactants for polymerase chain reaction (PCR) and other reactions such as ligase chain reaction, antibody binding reaction, oligonucleotide ligations assay, and hybridization assay. The sample can be subjected to thermal cycling.

The term "spectrally distinguishable species" as used herein refers to fluorescent dyes can be used to provide different colors that are at least spectrally distinguishable or spectrally distinct. Several dyes will be apparent to one skilled in the art of dye chemistry. One or more colors can be collect for each dye to provide identification of the dye or dyes detected. The dye can be a dye-labeled fragment of nucleotides. The dye can be marker triggered by a fragment of nucleotides. The dye can provide identification of components of the sample by association, for example, bonding to or reacting with a detectable marker, for example, a respective dye and quencher pair. The respective identifiable component can be positively identified by the fluorescence of the dye. The dye can be normally quenched, that can become unquenched in the presence of a particular target component in the sample. The fluorescent dyes can be selected to exhibit respective and, for example, different, excitation and emission wavelength ranges. The dye can be measured to quantitate the components. The dye can be detected in real-time to provide information about the identifiable components throughout the reaction. Examples of dye with desirable excitation and emission wavelengths can include 5-FAM™, SYBR Green, TET™, VIC™, JOE, TAMRA, NED, ROX, CY3, Texas Red, CY5, etc. The present teaching applies at least to red dyes, green dyes, and blue dyes.

According to various embodiments, the DNA in a sample at a particular stage of PCR can be analyzed by filtering light from the light source to permit only the wavelengths close to the excitation wavelength to impinge the sample. Further improvement can be achieved by filtering the light emitted from the sample so that only wavelengths close to the peak emission wavelength of a particular dye reach the detector.

According to various embodiments, the present teachings can provide at least one optical device, where each optical device includes a specific beamsplitter and a specific set of filters, such as excitation and emission filters, to provide an accurate analysis of DNA in a sample at various stages of PCR. The excitation filter in the set of filters can be chosen to allow wavelengths of light received from the light source that are close to the excitation wavelength of a predetermined dye to pass. The excitation filter can also be configured to block wavelengths of light that are greater than and/or less than the excitation wavelength. Similarly, the emission filter in the set of filters can be chosen to allow light close to the emission wavelength to pass while also blocking wavelengths greater than and/or less that the emission wavelength.

According to various embodiments, the present teachings can provide unique optical devices for each dye. This allows better sensitivity than if only one optical device is used for multiple dyes. Unique optical devices for each dye allows the excitation and emission wavelengths to be closer together than if a common optical device is used for all dyes. For example, unique excitation and emission filters for each dye allow the wavelengths of the excitation beam and emission beam to be closer together than if a common excitation filter was shared across multiple emission filters. The closer the wavelength of light of the excitation beam to the excitation wavelength of the sample, the greater the intensity of the fluorescence emission. Also, the closer the excitation wavelength is to the emission wavelength, the greater the intensity of the fluorescence emission. Higher emission intensity permits smaller concentrations of fluorescent material to be detected, and thus, the device can have an improved overall sensitivity. Further, using a beamsplitter that is unique to each optical device can add additional filtering of light at both the excitation and emission wavelengths and reduce unwanted noise at the wrong wavelength. Further, using unique excitation and/or emission filters close to the peak excitation and/or emission wavelengths separately or in combination with a light blocker reduces the errors that can result from temperature changes.

According to various embodiments, as illustrated in FIG. 1, fluorometry device 100 can include a light source 105, optical devices 110, a movable platform 115, a sample region 120, a detector 125, a focusing lens 130, a light blocker 135, and a motor 140. One example of the general arrangement of these components will now be described.

Light source 105 emits a source beam 107 that is received by one of the optical devices 110. For ease of illustration, FIG. 1 shows one optical device on movable platform 115. However, any number of optical devices can be installed on movable platform 115. A motor 140 is also attached to movable platform 115 with a stem 145. Motor 140 is used to move the movable platform 115 to interpose one of the optical devices 110 into the path of the source beam 107. The motor 140 can also move the movable platform 115 to interpose the light blocker 135 to prevent the source beam 107 from reaching the sample region 120.

The optical device 110 receives the source beam 107 and directs a portion as an excitation beam 121 through the focusing lens 130 to the sample region 120, where it impinges an array of samples 122. The excitation beam 121 causes one or more dyes in the samples 122 to fluoresce and emit light in the form of an emission beam 123.

The emission beam 123 is received by the optical device 110 and is then directed by the optical device 110 to a detector 125. The detector 125 generates a data signal that includes information that is representative of the concentration of DNA in the samples 122.

According to various embodiments, the light source can be LEDs used to provide improved illumination wavelength uniformity, light power output uniformity, and minimal degradation of output over extended periods of time. Further, LEDs operate at relatively low temperatures and require little or no external cooling. In some embodiments, the size of the light emitted from the light source 105 can be adjusted to be as small as possible to maximize the energy density directed onto the samples 122.

Figure 2:
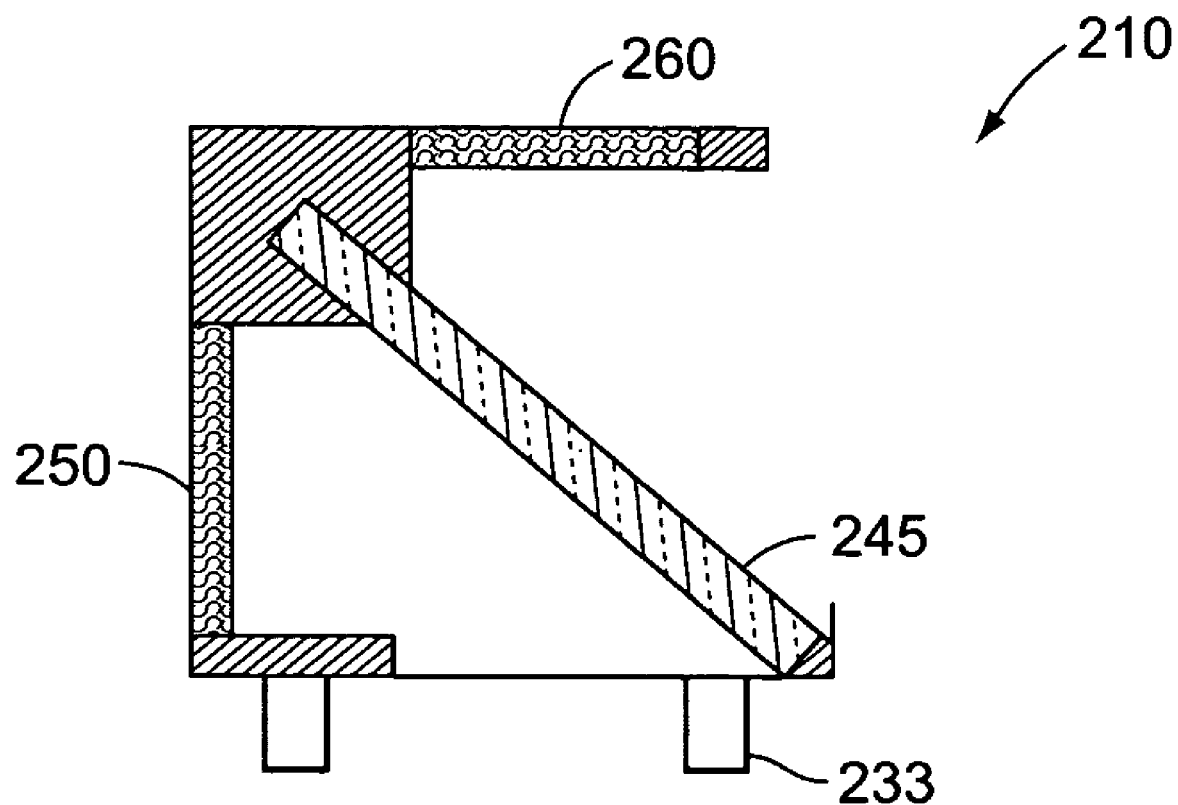
FIG. 2 illustrates a representative optical device.

According to various embodiments, as illustrated in FIG. 2, optical device 210 can include alignment pins 233, a beamsplitter 245, an excitation filter 250, and an emission filter 260.

According to various embodiments, alignment pins 233 ensure that optical device 210 can be precisely installed onto the movable platform 115, and thus, allow device 100 to easily interchange optical devices 110. Different optical devices can be removed and replaced through an access hatch in the instrument case (not shown) for device 100. For example, in some embodiments, one or more of the optical devices 110 attached to the movable platform can be tailored to measure the concentration of DNA based on particular dyes. However, if other dyes are used, alignment pins 233 allow device 100 to easily use other optical devices that are tailored to these other dyes. An optical device 110 can be removed from the movable platform 115; and a new optical device, such as optical device 210, can then be installed onto movable platform 115 using alignment pins 233 to ensure proper positioning.

The process of aligning optical device 210 can include positioning the alignment pins 233 into one or more sets of holes (not shown in FIG. 2) in movable platform 115. In order to confirm that optical device 210 is properly positioned, a fluorescent target that has known characteristic excitation and emission wavelengths, such as a dye exposed to DNA, can be placed in the sample region 120. The optical device 210 and/or the movable platform 115 can then be moved, for example in small increments, such that the detector 125 detects the maximum amount of light emitted from the fluorescent target. The position of the optical device 210 and/or the movable platform 115 is then recorded. This process can be repeated for any combination of optical devices and fluorescent targets. Alternatively, the optical device 210 can be aligned using a reference mirror (not shown) and one or more auto-collimators.

Accordingly, alignment pins 233 assist in installing and aligning optical devices 110 in device 100. Prior devices required continual re-alignment and disassembly of the device. These prior devices also required mechanical gauges or special tools to align the optical device and to re-assemble the device. In contrast, the optimal alignment position for each optical device 110 can be known using alignment pins 233 and the optical devices 110 can be easily and quickly substituted without requiring re-alignment.

According to various embodiments, excitation filter 250 can be used to selectively pass one or more wavelengths of source beam 107. The excitation filter 250 can be mounted in optical device 210. The wavelengths passed by excitation filter 250 can be chosen to block wavelengths shorter than the excitation wavelength of a particular dye exposed to DNA at a particular stage in PCR. In some embodiments, the excitation filter 250 can block wavelengths shorter than the excitation wavelength of a particular dye exposed to DNA at a particular stage in PCR. Accordingly, the excitation filter 250 can ensure that the excitation beam 121 will be close to the characteristic excitation wavelength of a particular dye.

According to various embodiments, optical device 210 can include an emission filter 260. The emission filter 260 can be disposed in optical device 210 to receive the emission beam 123 before it reaches the detector 125. The emission filter 260 can be configured to block light having the excitation wavelength of a particular dye exposed to DNA at a particular stage in PCR and allow wavelengths of the emission wavelength and longer to pass. Accordingly, the emission filter 260 can ensure that the emission beam 123 reaching the detector 125 will be close to the characteristic emission wavelength of the dye.

According to various embodiments, beamsplitter 245 can be a dichroic or non-dichroic reflector positioned at 45 degrees. However, depending on the application, the beamsplitter 245 can be positioned at angles other than 45 degrees. According to various embodiments, beamsplitter 245 can be chosen to transmit wavelengths of light that are shorter than the excitation wavelength of a particular dye exposed to DNA at a particular stage of PCR. The beamsplitter 245 can also be chosen to reflect wavelengths that are at, or longer than, the excitation wavelength of a particular dye exposed to DNA at a particular stage of PCR. For example, the beamsplitter 245 can reflect wavelengths that are shorter than the characteristic wavelength. According to various embodiments, beamsplitter 245 can be a 50-50 partly silvered mirror.

Figure 3A:
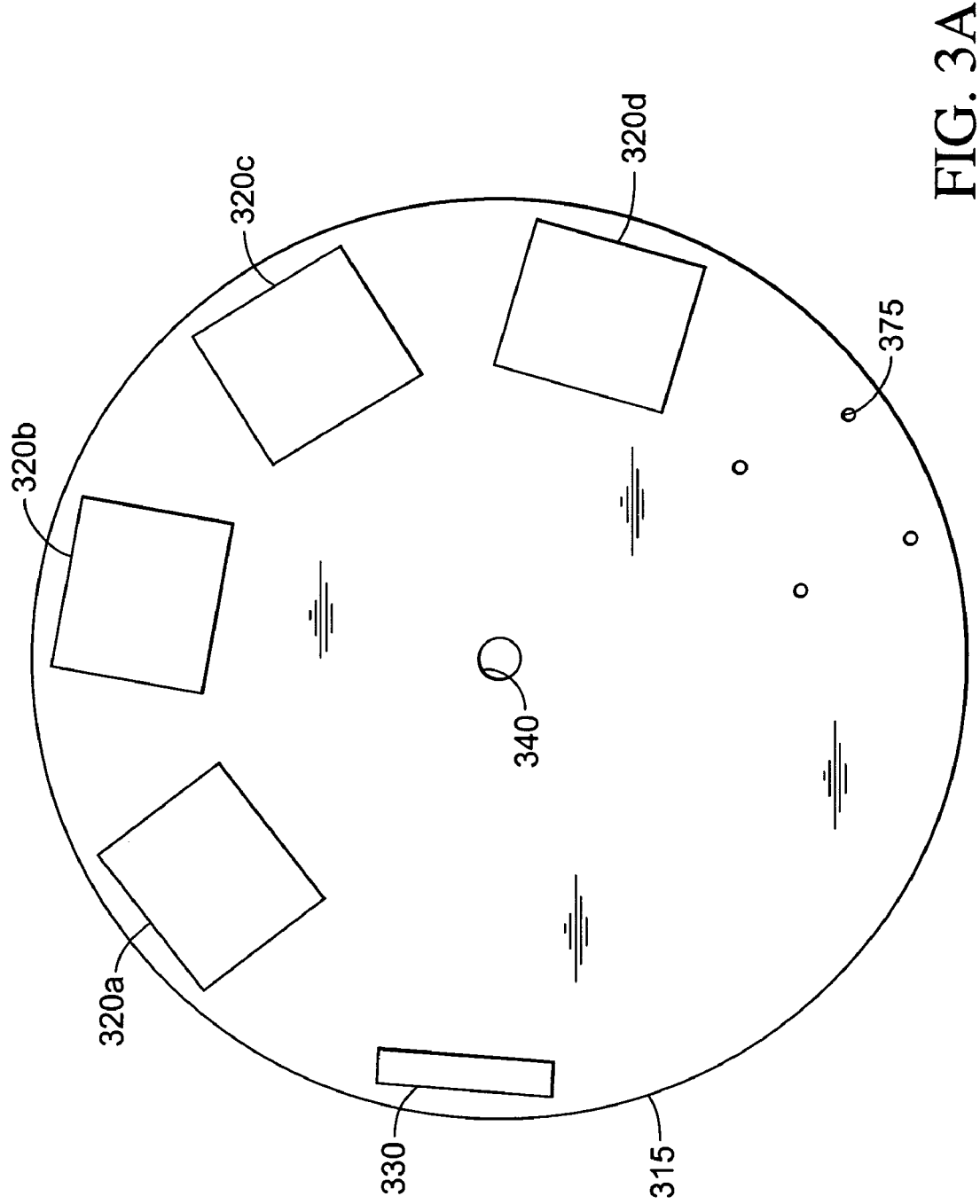
FIG. 3A illustrates a representative movable platform according to various embodiments of the present teachings.
Figure 3B:
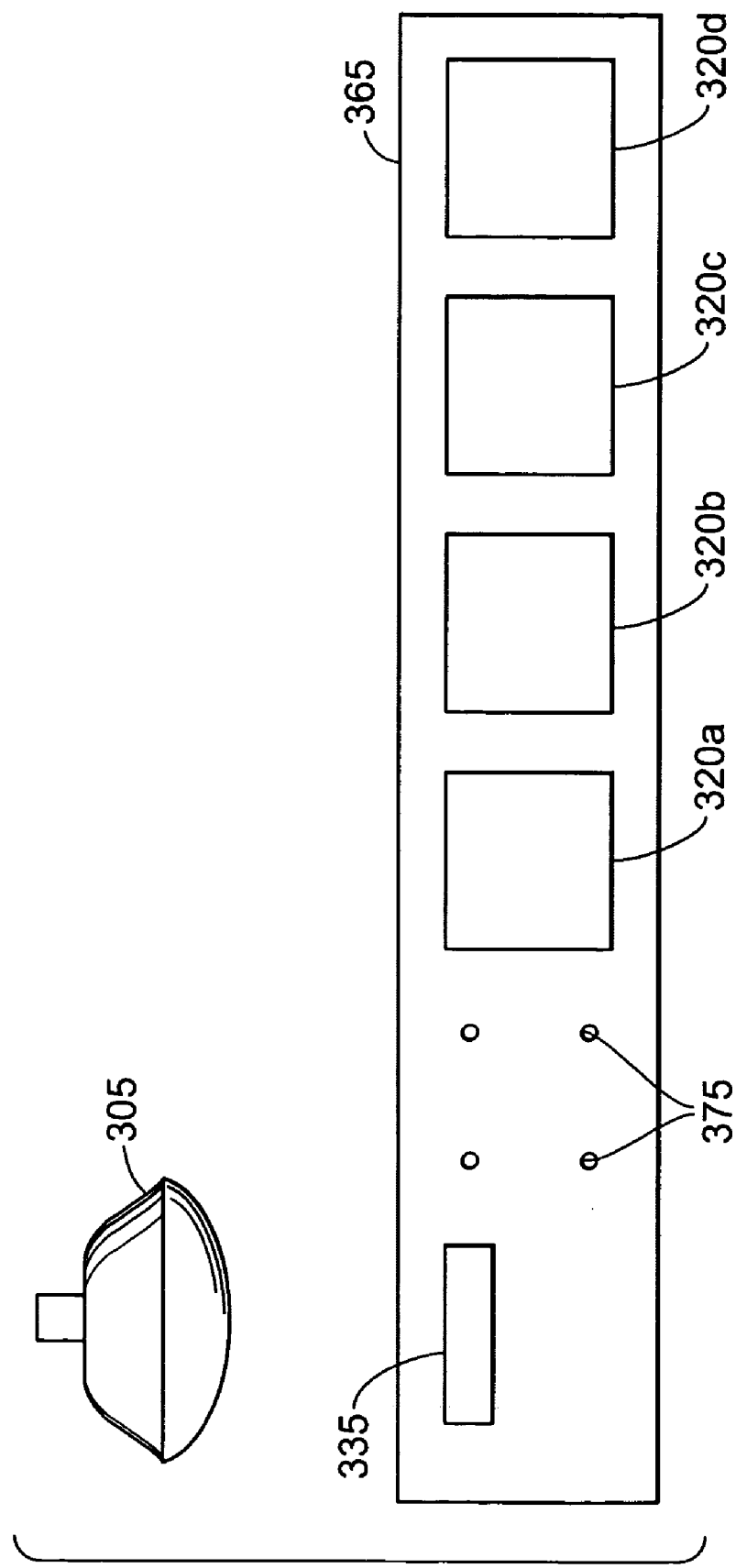
FIG. 3B illustrates a representative movable platform according to various embodiments of the present teachings.

According to various embodiments, as illustrated in FIGS. 3A and 3B movable platforms can be configured to provide circular and/or lateral movement. FIG. 3A depicts a rotatable movable platform 315 such as a turret or carrousel assembly. Rotatable movable platform 315 can be rotated to move the different optical devices 310a, 310b, 310c, and 310d to receive light from the light source 305 and to position light blocker 330 to block light from reaching the sample. The rotatable movable platform 315 can be generally circular, or any portion of a circle, so long as it can be rotated and can accommodate multiple attachments. For example, the rotatable movable platform 315 can accommodate multiple optical devices and a light blocker and can be rotated to position these attachments to receive light from the light source 305.

FIG. 3B depicts a linearly movable platform 365. Linearly movable platform 365 can be moved linearly to position different optical devices 310a, 310b, 310c, and 310d to receive light from the light source 305 and to position light blocker 335 to block light from reaching the sample. The linearly movable platform 365 can be any shape, such as rectangular, so long as it can accommodate multiple attachments and can be moved linearly to position the attachments to receive light from the light source 305.

According to various embodiments, movable platforms 315 and 365 can also include precision alignment pinholes 375, which are designed to receive alignment pins of an attachment, such as alignment pins 233 of optical device 210. As shown in FIGS. 3A and 3B, the precision alignment pinholes 375 can be holes formed in the movable platforms 315 and 365 and receive the precision alignment pins of the optical devices 310a-310d and the light blocker 335.

Now referring back to FIG. 1, sample region 120 provides a location for holding one or more of the samples 122. For example, sample region 120 can be structured as a tray or bracket that holds one or more vials of the sample 122.

Sample 122 can be an aqueous suspension of ingredients used for holding one or more "seed" samples of DNA. The aqueous suspension of sample 122 include selected DNA primer strands, DNA elements, enzymes, and other chemicals. During the PCR process, the sample 122 is thermally cycled, which causes the DNA sample to replicate itself.

According to various embodiments, detector 125 detects light, such as emission beam 123, emitted from the sample 122. According to various embodiments, detector 125 generates a signal indicating the amount or concentration of DNA present in sample 122 based on the light emitted from sample 122. For example, detector 125 can include one or more processing devices to generate the signal. According to various embodiments, detector 125 can be connected to a processing device that generates the signal.

According to various embodiments, lens 130 can be optionally included in device 100 to assist in focusing light, such as the excitation beam 107, onto sample region 120. Lens 130 can be constructed from known materials and have various refractory properties to focus light onto sample region 120. For example, some embodiments of the invention use a Fresnel lens for the lens 130.

According to various embodiments, light blocker 135 allows the device 100 to control when sample region is illuminated by the light source 105. Light blocker 135 can be useful because some dyes become spectrally unstable when they are exposed to changes in temperature, such as from the light source or from PCR. In particular, the peak excitation and emission wavelengths of a dye can "drift" or weaken when the dye is exposed to temperature changes. In prior devices, the light source required a warm-up time to stabilize. During this stabilization period, it is possible to photobleach the sample. Photobleaching weakens the emission spectrum from the dye and can result in the detector sensing an incorrect concentration of DNA.

According to various embodiments, light blocker 135 can be used in device 100 to allow light source 105 to be on continuously. Rather than using a separate mechanical or electronic shutter, device 100 can include a light blocker 135, such as a blocking plate, that is attached to the movable platform 115. Accordingly, the motor 140 can also be used to position the movable platform 115, such that the light blocker 135 blocks light from the light source 135.

According to various embodiments, motor 140 moves movable platform 115 into various positions to interpose optical devices 110 into the path of source beam 107. As shown in FIG. 1, motor 140 can be a direct-drive stepper motor. According to various embodiments, as illustrated in FIG. 3A, motor 140 that can be attached to movable platform 115 by the stem 145 that is mounted into a mounting hole 340. During operation, motor 140 rotates the rotatable movable platform 315 to position different optical devices 310a-310d or the light blocker 335 into and out of the optical path of the source beam.

According to various embodiments, motor 140 can be any motor that provides linear movement. For example, as shown in FIG. 3B, motor 140 can linearly move movable platform 365. For ease of illustration, the embodiments shown in FIGS. 3A and 3B include four optical devices. However, some embodiments of movable platforms 115, 315, and 365 can accommodate any number of optical devices.

Figure 4:
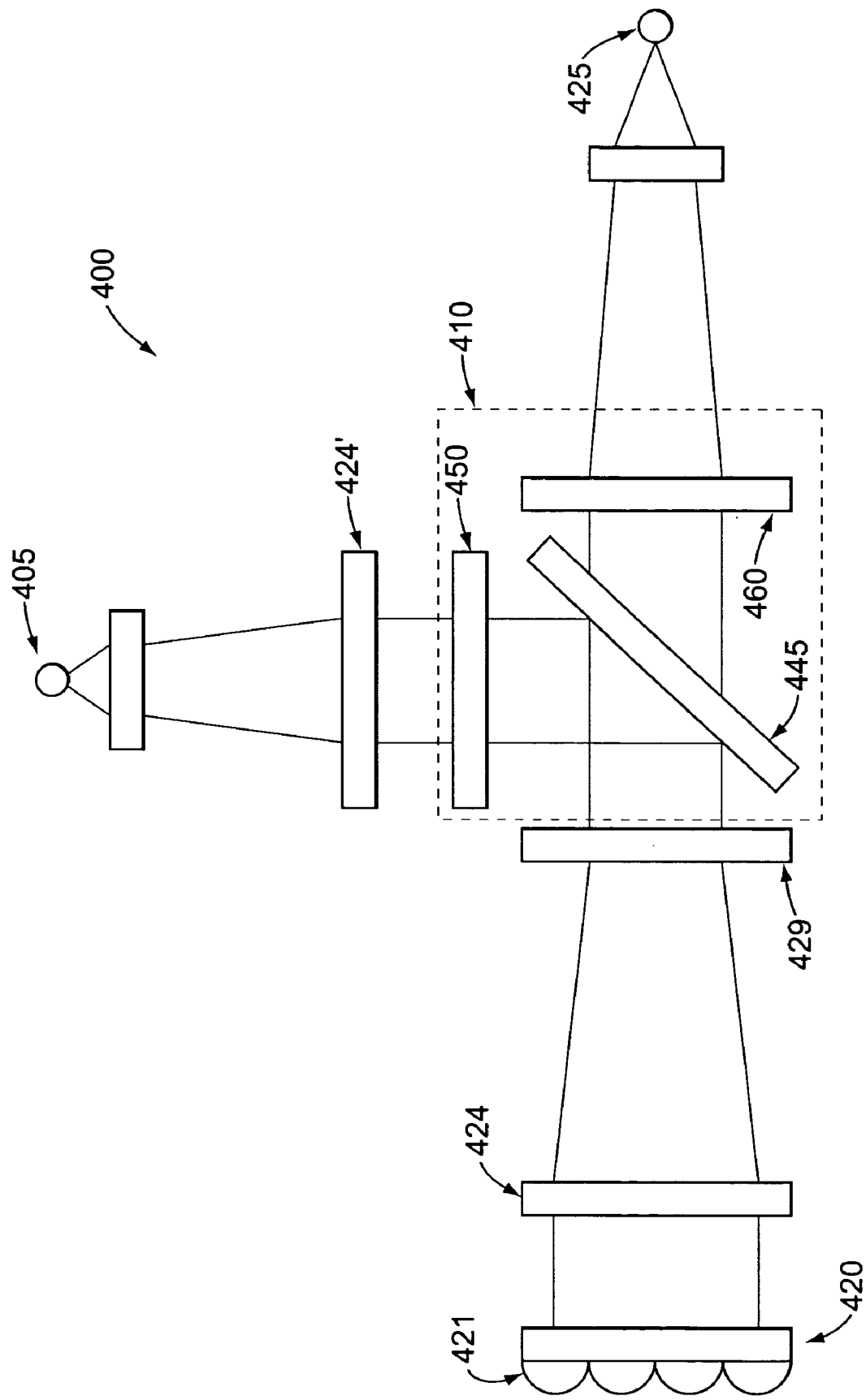
FIG. 4 illustrates another representative fluorometry system according to various embodiments of the present teachings.

According to various embodiments, there is an optical system 400, as shown in FIG. 4, comprising a light source 405, an optical device 410 (shown generally as the features surrounded by the dotted line), a sample region 420, and a detector 425. Light source 405, sample region 420, and detector 425 can be any of those as described herein. According to various embodiments, optical device 410 can comprise an optical device having structures similar to those described herein, such as an excitation filter 450, a beamsplitter 445, and an emission filter 460. Optical system 400 can also comprise a first optical element 424 and a second optical element 424', that may or may not be included in optical device 410.

According to various embodiments, first optical element 424 can comprise a mask, such as a Fresnel mask, that includes a plurality of apertures. Each aperture can be adjusted to reduce non-uniformities in light emitted from the samples in sample region 420, which can include sample wells 421. For example, the arrangement of an aperture, such as the size and/or shape of the apertures, can be adjusted. In general, the apertures can be adjusted so light from wells having a similar volume and a similar concentration of sample, and that use a similar die will pass through the mask having a similar light signal, such as a similar relative response. As such, the signal reaching detector 425 will be an accurate representation of the reaction.

For example, although a first well and a second well of a sample region may contain similar volumes and concentrations of sample material, and may also use similar dyes, the light from each of the first and second wells reaching the detector may not be similar. In various embodiments, a first aperture and a second aperture of the Fresnel mask can be positioned next to the first well and the second well, respectively, of sample region 420. The arrangement of the first and second apertures can be adjusted so that non-uniformities in the light from the first and second wells that reach the detector can be reduced.

According to various embodiments, the first optical element 424 can comprise a plurality of lenses with each of the plurality of lenses having a unique numerical aperture (NA). The NA of the lenses, as well as the position of the lenses, can be adjusted to reduce the non-uniformities in light emitted from the samples in the wells of the sample region 420. In some embodiments, the lenses can be molded to have the unique NA. In general, the NA can be adjusted so light from wells having a similar volume and a similar concentration of sample material, and that use a similar die, will pass through the mask having a similar light signal. As such, the signal reaching detector 425 can be an accurate representation of the reaction.

According to various embodiments, the optical system can further comprise an additional filter 429, such as a neutral density filter, that can vary the transmission of the emitted sample light. For example, additional filter 429 can vary the transmission based on the position of wells in sample region 420.

According to various embodiments, optical system 410 can further comprise a second optical element 424'. Second optical element 424' can comprise a Fresnel mask, a neutral density filter, or a lens having a predetermined NA. Including second optical element 424' aids in reducing non-uniformities in the light from light source 410. Second optical element 424' can be positioned to reduce non-uniformities in the light from light source 405 before the light reaches the sample region 420.

According to various embodiments, the type of adjustment to optical elements 424 and 424' can be determined using any of a variety of techniques either separately or in combination. Exemplary techniques include sequential ray trace models, non-sequential ray trace models, radiometric formulae, empirical measurements of light reaching the sample space, and empirical measurements of light reaching the detector.

According to various embodiments, light is emitted from light source 405 and passes through excitation filter 421 and optionally through second optical element 424' before impinging on beamsplitter 445. A portion of the light impinging on beamsplitter 445 is directed to the samples in sample region 420 where it causes the samples to luminesce. The light emitted from the samples is passed through first optical element 424 and optionally through further filter 429. The light is directed through filter 427 and detected by detector 425.

Figure 5A:
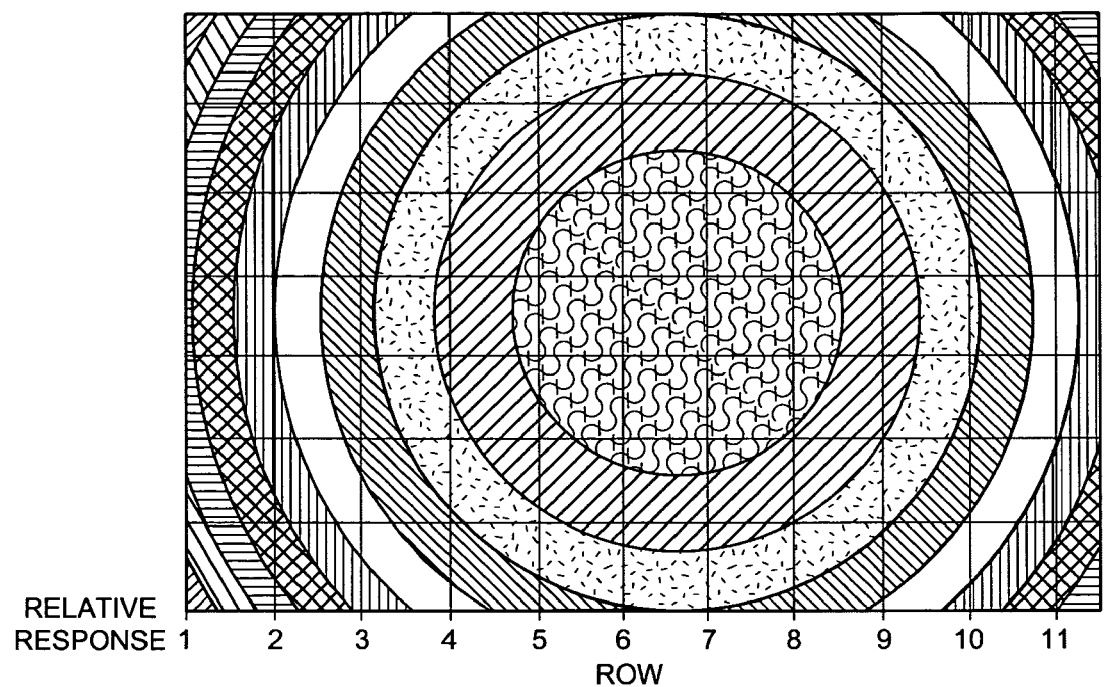
FIG. 5A depicts an exemplary spatial response profile.
Figure 5B:
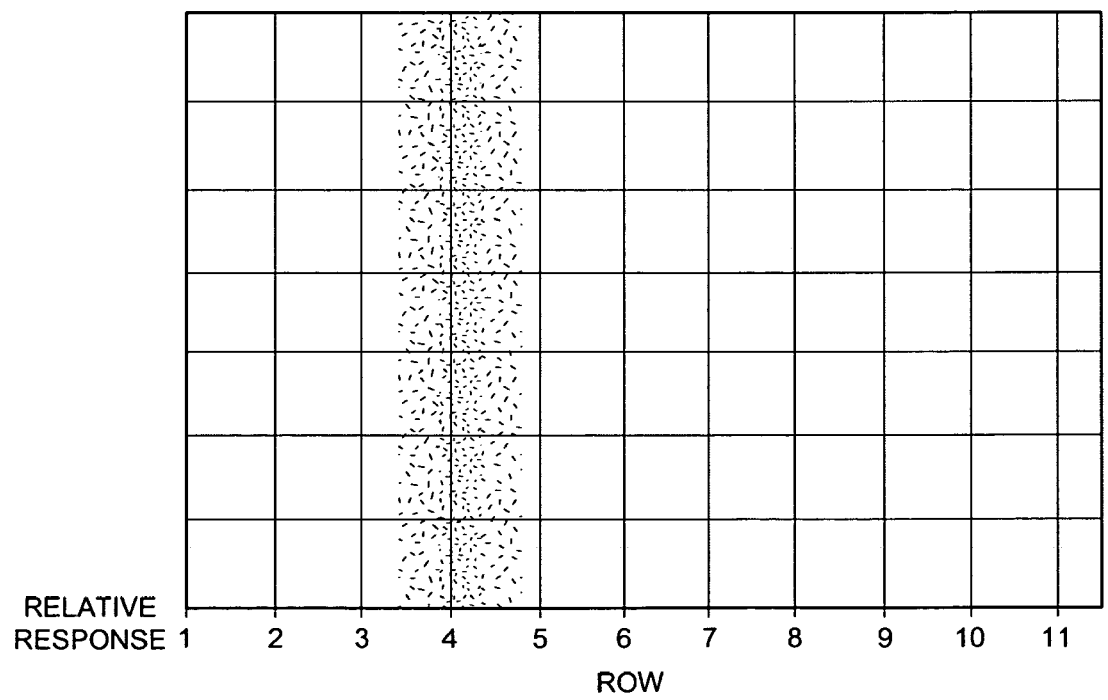
FIG. 5B depicts another exemplary spatial response profile.

FIG. 5a depicts an exemplary spatial response profile when optical systems do not use the optical elements as described herein. As can be seen in FIG. 5a, the sample light contains numerous bands of varying intensity. In various embodiments, the varying bands correspond to the non-uniformities in the light emitted from the samples in sample region 420 and/or the light emitted from light source 405. FIG. 5b depicts an exemplary spatial response profile when optical systems use optical elements as described herein. As can be seen in FIG. 5b, the sample light is relatively homogeneous when the optical elements are used.

Figure 6:
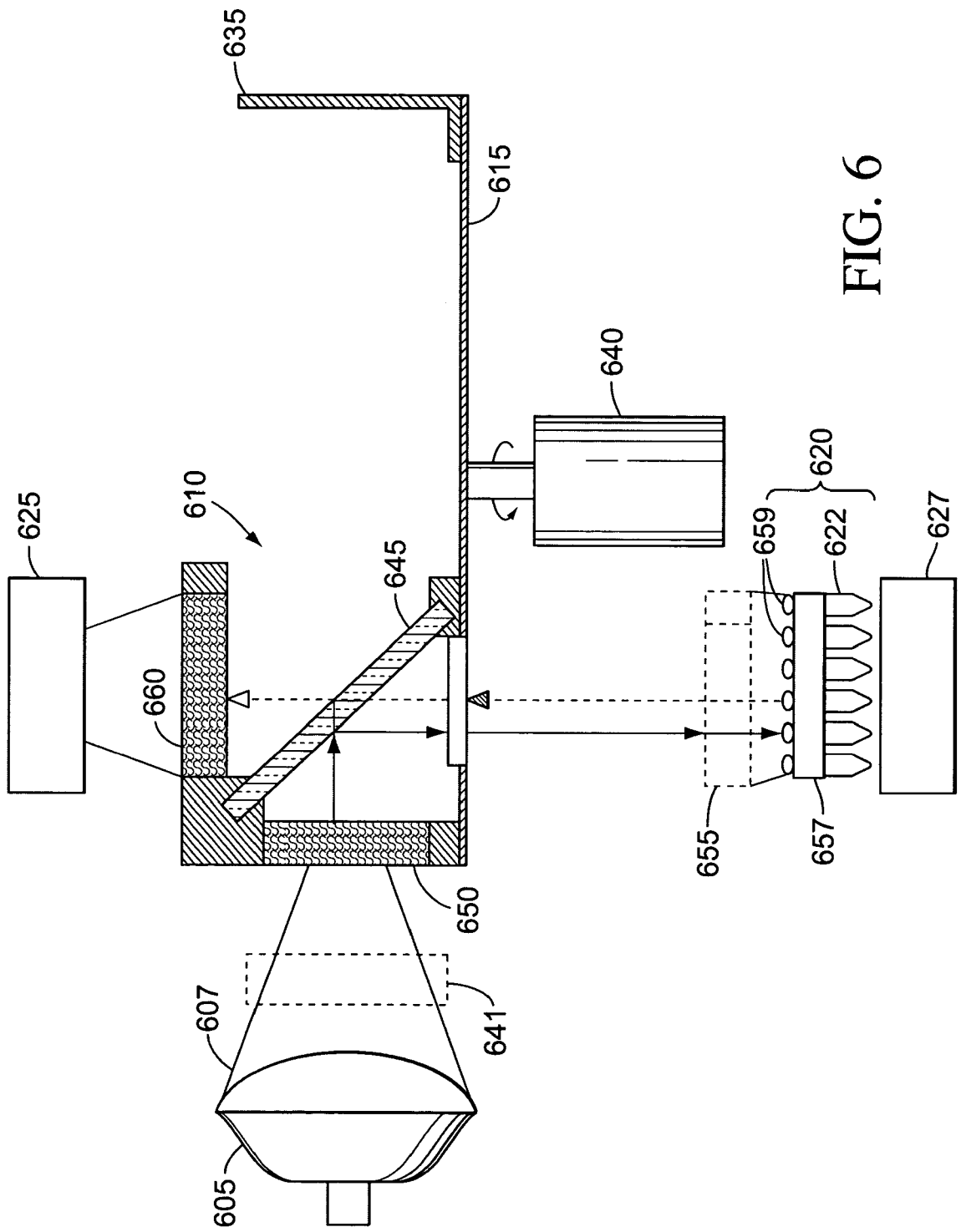
FIG. 6 illustrates the operation of a representative fluorometry system according to various embodiments of the present invention.

According to various embodiments, the operation of device 100 will now be described with reference to FIG. 6. As shown in FIG. 6, some embodiments of the invention operate by allowing the light source 605, such as an illumination lamp or LED, to warm to a steady state temperature. The motor 640 positions the light blocker 635 attached to the movable platform 615 to block the source beam 607 from reaching the sample region 620. The light blocker 635 can be positioned in front of source beam 607 before the light source 605 is turned on or before the sample 622 is placed in the sample region 620. The sample 622 is then temperature cycled, using the temperature controller 627 to initiate the PCR process. At the appropriate time of interest during PCR, the motor 640 moves the movable platform 615 to position the first of a plurality of optical devices 610 to receive the source beam 607. An infra-red (IR) hot mirror filter 641 optionally can be placed between the light source 605 and the optical device 610. Further, an optical element (not shown) can be positioned to receive the source beam 607.

The source beam 607 goes through the IR hot mirror filter 641 and is received by the excitation filter 650. The source beam reflects off of the beamsplitter 645 and is directed to the sample region 620. An optical element 655 and/or an additional filter (not shown) can be placed between the beamsplitter 645 and the sample region 620. Additionally, the multiple samples can be held in a sample region 657 that optionally can include well lenses 659 positioned each sample 622. Well lenses 659 act to focus the light onto the sample 622. Wavelengths of light emitted by the light source 605 that are shorter than the excitation wavelength of the particular dye exposed to DNA at the appropriate time of PCR are blocked by the excitation filter 650 and/or transmit through the beamsplitter 645. Light that impinges the sample 622 is shown as a solid line in FIG. 6 with solid arrowheads and can be referred to as the excitation beam.

The excitation beam then causes dyes exposed to DNA in the sample 622 to emit or fluoresce light. Light emitted from the sample 622, shown as a broken line with hatched arrowheads in FIG. 6, transmits through the well lens 659, the optical element lens 655, the beamsplitter 645, and the emission filter 660. Undesired wavelengths of light emitted from the sample 622 are reflected by the beamsplitter 645 or are blocked by the emission filter 660. The portion of the emitted light that transmits through the beamsplitter 645 and emission filter 660 is received by the detector 625, such as a camera or CCD camera. This transmitted light is shown with a broken line with non-shaded arrowheads in FIG. 6 and can be referred to as the emission beam.

According to various embodiments, sample region 657 that holds the sample 622 can include vials typically formed conically in a plastic unitary tray. The plastic tray can contain a plurality of vials, for example 96 vials in an array of 12 by 8, to hold multiple samples. The tray can be removed from the system for sample preparation. A plastic unitary cover with caps for the vials can rest on or attach to the vials to prevent contamination or evaporation loss. Other systems can be used for this function, such as oil on the top of the sample surface, in which case caps are not needed. If caps are used, they can be transparent to light used by the instrument and can be convex facing upwardly from the sample. A platen (not shown) can optionally rest over the vial caps or, if no caps are used, then directly over the vials. The platen, which can be made of metal, can have an array of holes aligned with the vials. Each hole can have a diameter about the same diameter as the vial top diameter. If there are caps, the platen can have its temperature maintained by a film heater or other device to heat the platen. Heating the platen helps to prevent condensation under the caps without interfering with DNA replication in the vials. For example, the platen can be held at a temperature slightly higher than the highest sample temperature that the thermal cycle reaches.

According to various embodiments, the present teachings provide impinging the excitation beam on sample region 657 and generating a fluorescent image from the plurality of samples 622. This permits the detector 625 to generate a data signal representative of the DNA in the samples at the particular stage of PCR.

At the next appropriate time of interest in PCR, after the detector 625 generates the data signal that results from the first optical device 610 receiving the source beam 607, the motor 640 moves the movable platform 615 to position another one of the plurality of optical devices 610 (not shown) to receive the source beam 607. The other one of the plurality of optical devices receives the source beam 607 and the process detailed above is repeated. The above processes can be repeated for each appropriate time of interest in PCR.

After the dye colors of interest are measured, the movable platform 615 can be moved to position the light blocker 635 to block the source beam 607. The samples 622 can then be temperature cycled to prepare them for the next detection or until all desired detection has been completed.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An optical device for fluorometry to monitor a biological sample, the device comprising:
   a first filter to condition an excitation light directed at a sample region;
   a beamsplitter positioned along a first optical axis, the first optical axis being an optical axis of the excitation light, and the beamsplitter positioned along a second optical axis, the second optical axis being an optical axis of an emission light; and
   a first optical element positioned along the second optical axis to collimate the emission light and to reduce non-uniformities in the emission light prior to the emission light impinging the beamsplitter, wherein the first optical element comprises a plurality of lenses, and wherein the first optical element is positioned proximate to the sample region comprising a plurality of wells, and further wherein each of the plurality of lenses being proximate to a corresponding well, and wherein a numerical aperture of each of the plurality of lenses depends on a position of the corresponding well.

2. An optical device for fluorometry to monitor a biological sample, the device comprising:
- a first filter to condition an excitation light directed at a sample region;
- a beamsplitter positioned along a first optical axis, the first optical axis being an optical axis of the excitation light, and the beamsplitter positioned along a second optical axis, the second optical axis being an optical axis of an emission light; and
- a first optical element positioned along the second optical axis to collimate the emission light and to reduce non-uniformities in the emission light prior to the emission light impinging the beamsplitter, wherein the first optical element comprises a neutral density filter, and wherein the first optical element is positioned proximate to the sample region comprising a plurality of wells, and further wherein the transmisivity across the neutral density filter varies according to the position of the neutral density filter relative to the wells in the sample region.

3. An optical device for fluorometry to monitor a biological sample, the device comprising:
- a first filter to condition an excitation light directed at a sample region;
- a beamsplitter positioned along a first optical axis, the first optical axis being an optical axis of the excitation light, and the beamsplitter positioned along a second optical axis, the second optical axis being an optical axis of an emission light; and
- a first optical element positioned along the second optical axis to collimate the emission light and to reduce non-uniformities in the emission light prior to the emission light impinging the beamsplitter, wherein the first optical element is adjusted to reduce non-uniformities in the emission light according to at least one of a sequential raytrace model, a non-sequential raytrace model, a radiometric formulae, and an empirical measurement of emission light reaching an image sensor.

4. An optical device for fluorometry to monitor a biological sample, the device comprising:
- a first filter to condition an excitation light directed at a sample region;
- a beamsplitter positioned along a first optical axis, the first optical axis being an optical axis of the excitation light, and the beamsplitter positioned along a second optical axis, the second optical axis being an optical axis of an emission light; and
- a first optical element positioned along the second optical axis to collimate the emission light and to reduce non-uniformities in the emission light prior to the emission light impinging the beamsplitter; and
- a second optical element positioned to collimate the excitation light and to reduce non-uniformities in the excitation light prior to the excitation light impinging the beamsplitter, wherein the second optical element is adjusted to reduce non-uniformities in the excitation light according to at least one of a sequential raytrace model, a non-sequential raytrace model, a radiometric formulae, and an empirical measurement of excitation light reaching the sample region.

5. A method of fluorometry to monitor a biological sample comprising:
- providing a sample region comprising a sample tray and a plurality of wells, wherein each of the wells includes a sample;
- providing a first filter to condition an excitation light;
- providing a first optical element;
- reducing non-uniformities in an emission light of the samples;
- impinging a detector with uniform emission light for samples in different wells that have a similar volume of material, a similar concentration of material, and a similar dye, wherein the first optical element comprises a plurality of lenses, each of the plurality of lenses being proximate to a corresponding well, wherein each lens has a numerical aperture adjusted based on the position of the corresponding well to which the particular lens is proximate; and
- generating a data signal representative of the emission light impinging on the detector.

6. A method of fluorometry to monitor a biological sample comprising:
- providing a sample region comprising a sample tray and a plurality of wells, wherein each of the wells includes a sample;
- providing a first filter to condition an excitation light;
- providing a first optical element;
- reducing non-uniformities in an emission light of the samples;
- impinging a detector with uniform emission light for samples in different wells that have a similar volume of material, a similar concentration of material, and a similar dye, wherein the first optical element comprises a neutral density filter, wherein a transmisivity across the neutral density filter varies according to a position of the neutral density filter relative to the wells; and
- generating a data signal representative of the emission light impinging on the detector.

7. A method of fluorometry to monitor a biological sample comprising:
- providing a sample region comprising a sample tray and a plurality of wells, wherein each of the wells includes a sample;
- providing a first filter to condition an excitation light;
- providing a first optical element;
- reducing non-uniformities in an emission light of the samples;
- impinging a detector with uniform emission light for samples in different wells that have a similar volume of material, a similar concentration of material, and a similar dye, wherein the first optical element is adjusted to reduce non-uniformities in the emission light according to at least one of a sequential raytrace model, a non-sequential raytrace model, a radiometric formulae, and an empirical measurement of emission light reaching an image sensor; and
- generating a data signal representative of the emission light impinging on the detector.

8. A method of fluorometry to monitor a biological sample comprising:
- providing a sample region comprising a sample tray and a plurality of wells, wherein each of the wells includes a sample;
- providing a first filter to condition an excitation light;
- providing a first optical element;
- providing a second optical element to reduce non-uniformities in the excitation light;
- reducing non-uniformities in an emission light of the samples;
- impinging a detector with uniform emission light for samples in different wells that have a similar volume of material, a similar concentration of material, and a similar dye, wherein the second optical device is adjusted to reduce non-uniformities in the excitation light according to at least one of a sequential raytrace model, a non-sequential raytrace model, a radiometric formulae, and an empirical measurement of excitation light reaching the sample tray; and generating a data signal representative of the emission light impinging on the detector.

* * * * *